United States Patent [19]

Hoisington

[11] 4,078,311

[45] Mar. 14, 1978

[54] DENTAL HYGIENE DEMONSTRATION APPARATUS

[76] Inventor: William C. Hoisington, 210 Lake Wash. Blvd., Seattle, Wash. 98112

[21] Appl. No.: 617,670

[22] Filed: Sep. 29, 1975

[51] Int. Cl.$^2$ ............................................. A61C 19/00
[52] U.S. Cl. .......................................... 32/71; 35/49
[58] Field of Search ................. 35/22 A, 29 E, 23 R, 35/49; 32/71, 1, 2, 11; 132/93, 79 E, 84 R

[56] References Cited

U.S. PATENT DOCUMENTS

| | | | |
|---|---|---|---|
| 1,598,052 | 8/1926 | Choyes | 32/71 |
| 2,060,869 | 11/1936 | Hopkins | 32/49 |
| 2,333,795 | 11/1943 | Kellerman et al. | 32/71 |
| 3,458,936 | 8/1969 | Schulz et al. | 32/71 |
| 3,581,408 | 6/1971 | Mobier | 35/22 |
| 3,771,227 | 11/1973 | Black | 32/71 |
| 3,942,539 | 3/1976 | Corliss et al. | 132/79 E |

*Primary Examiner*—John F. Pitrelli
*Assistant Examiner*—Mickey Yu
*Attorney, Agent, or Firm*—Christensen, O'Connor, Garrison & Havelka

[57] ABSTRACT

The apparatus and technique enable an instructor, for example, an elementary grade school teacher, to simulate good and band dental hygiene conditions, including the presence of plaque between the teeth and the removal of the same with flossing; the presence of plaque in the periodontal recesses in the tissue around the bases of the teeth and the removal of the same with proper brushing; and the results of failing to brush and/or floss, including the enlargement of the recesss and the ultimate condition in which one or more of the teeth loses its lateral support and becomes wobbly, or is susceptible to being lost altogether. The apparatus and technique also enable the instructor to demonstrate the various skills necessary to proper brushing and flossing, including the skill of "easing" the floss through each of the contact points between pairs of teeth, to avoid injury to the gum tissue below, and the skill of "wrapping" the floss about the contour of each tooth, to remove the widest possible band of plaque. Using the same apparatus that the instructor used in the simulation and demonstration steps, the student can practice and develop his brushing and flossing skills, and he can do so in stages, for ease of understanding.

24 Claims, 6 Drawing Figures

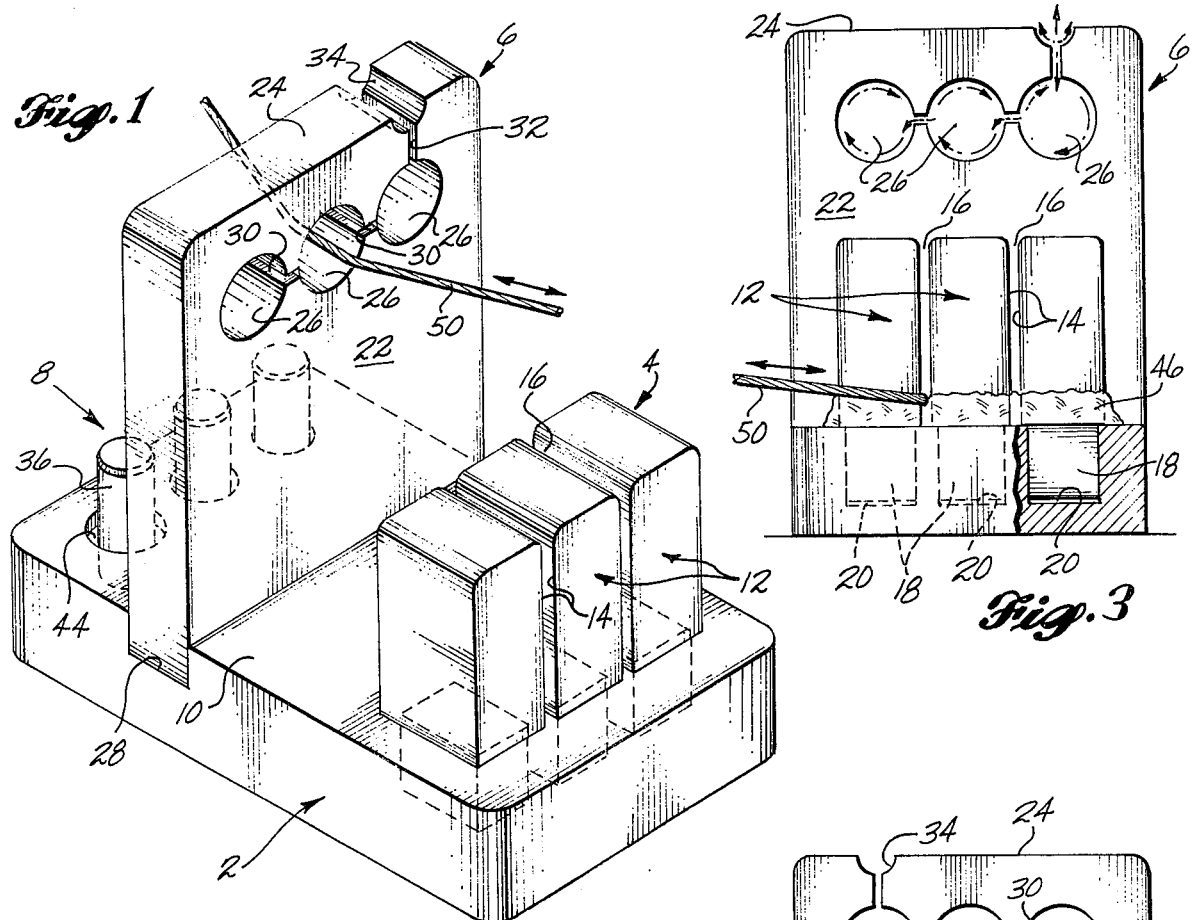
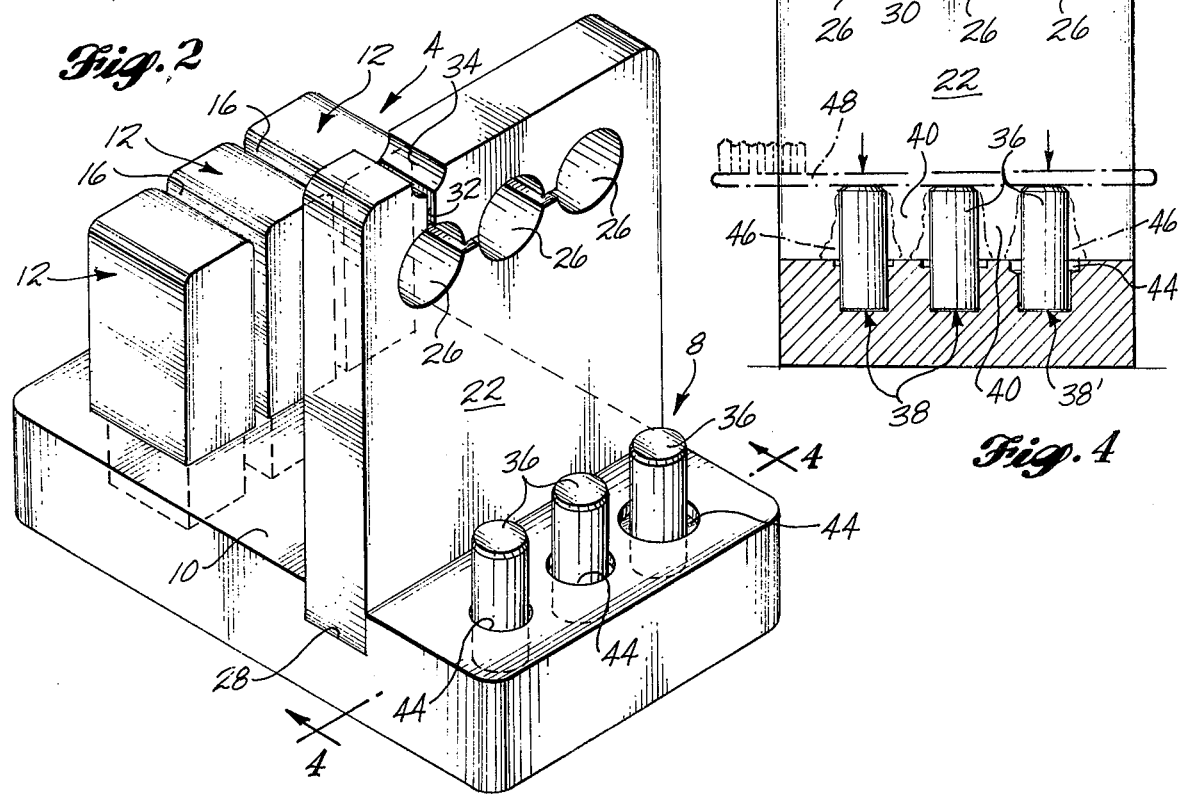

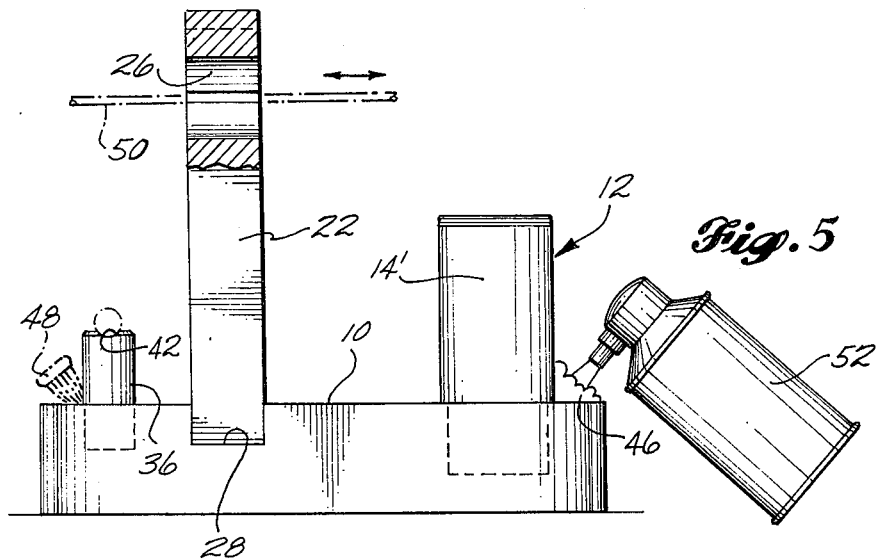
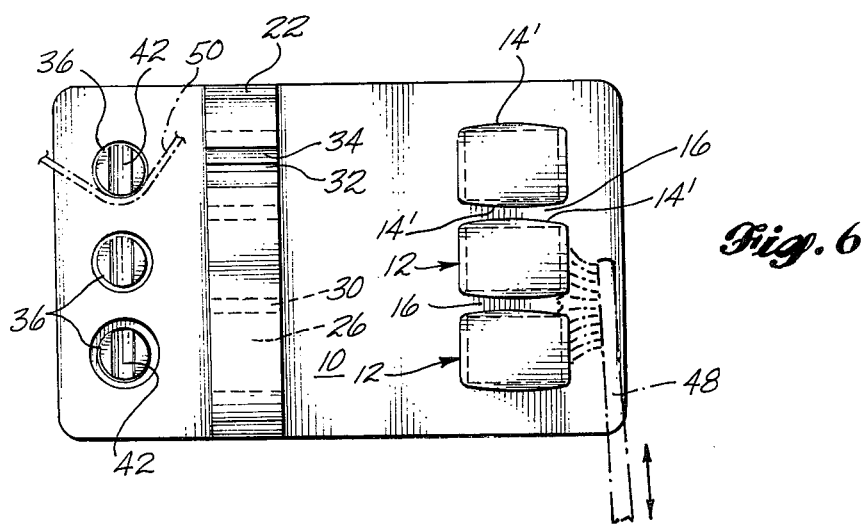

DENTAL HYGIENE DEMONSTRATION APPARATUS

RELATED APPLICATION

This application is related to United States Design patent application Ser. No. 617,669, filed Sept. 29, 1975 by the inventor herein.

THE INVENTION IN GENERAL

Human teeth are embedded in the bones of the jaw and are aligned in rows with the opposing surfaces of each pair of teeth spaced apart from one another, but also making point contact with one another where their convex curvatures meet. The jaw bones and the basal portions of the teeth are covered by a tough fibroelastic tissue which, though attached securely to the bones and to the basal portions, is slightly offset from the exposed portions of the teeth, to form a slight moat-like periodontal recess around the base of each tooth. Bacterial plaque forms on the teeth, and in and about the recesses in the tissue therearound, and this plaque is etiologic for both cavities and periodontal diseases. A toothbrush can be used to dislodge the plaque on the inside and outside faces of the teeth, and from within the periodontal recesses in the tissue about the bases thereof. But a toothbrush will not reach between the teeth and remove the plaque from the opposing surfaces thereof. Consequently, most periodontal disease starts between the teeth, and most cavities occur there. Therefore, in addition to brushing, complete and thorough dental hygiene requires that dental floss be employed to dislodge the plaque between the teeth, including the plaque on the opposing surfaces thereof.

In using the floss, the recommended technique is to grasp it in both hands, wind it about a finger in each hand, and then while using the thumbs and fingers to draw the intermediate length taut, to "saw" the length into the slot between each pair of teeth, and through the contact point of that pair. Thereafter, the sawing motion is continued below the contact point to scrape and dislodge the plaque on first one of the opposing surfaces, and then on the other, whereafter the length of floss is sawed upwardly through the contact point and out of the slot.

The recommended technique for brushing is to angle the brush at roughly 45° to the teeth, so that in oscillating it relative to the teeth, the bristles will operate to dislodge and remove the plaque from in and about the recesses in the tissue at the bases thereof. If the plaque is not removed on a consistent basis, it may break down the tissue, and produce a further offset of the same from the bases of the teeth, thus producing a widening and deepening of the recesses. When this happens, the brush cannot be used to completely remove the plaque, even when the brush is properly angled to the teeth. Ultimately, a serious detachment can occur, which along with the bone loss can effectively remove the lateral support for one or more of the teeth, so that the tooth becomes loose and will wobble on the jaw. In such a case, corrective action must be taken by the dentist, including splinting the loose tooth to a firmly attached tooth further along the length of the row of teeth. Usually, the splint is set in a series of indentations in the tops of the teeth.

The present means and technique enables an instructor, such as an elementary grade school teacher, to teach and develop in his students an awareness of the necessity for flossing and proper brushing of the teeth. Also, it enables him to allow the student to practice and develop his skills on the same means which the instructor has employed in pointing up the necessity for flossing and brushing. The present means and technique also enables the instructor to develop this awareness in stages, that is, to demonstrate the necessity for flossing and proper brushing in separate stages, and also to demonstrate the consequences of failing to floss or to brush properly. The means and technique also enable the student to practice and develop his skills in stages, and to follow the same sequence of stages as the instructor follows in his demonstrations.

Moreover, the demonstrations produce a visual awareness in the student, inasmuch as the means and technique operate to simulate the bacterial plaque on the teeth, and in and about the recesses in the tissue, and enable the instructor to demonstrate both the result achieved when flossing and brushing are done properly, and the result achieved when either or both is omitted or done improperly.

Furthermore, the student can develop the full range of skills needed in brushing and flossing, including the skill of "easing" the floss through each contact point to avoid injury to the gums. In short, when the student turns to his own teeth, he will have experienced all aspects of each task, and will have developed all of the skills necessary to accomplish the task.

For example, the student actually sees the problem in using a brush alone, without flossing, and he gets an opportunity to practice flossing in several stages, including a stage in which he practices "easing" the floss through each contact point. He also sees that he must "wrap" the floss about the contour of each tooth, to do a complete and thorough job; and he gets an opportunity to practice doing so, and to practice under conditions simulating those in the mouth, that is, simulating the crowded and cramped conditions. The student also sees the problem which arises when the brush is not angled properly to the teeth, and he gets an opportunity to practice under conditions simulating the tissue conditions in the mouth. He also sees what happens, when the failure to brush, or to brush properly, produces a condition in which one or more of the teeth loses its lateral support, and becomes loose, or is susceptible to being lost. And, finally, he sees what the dentist must do to correct this condition, including the step of splinting from the loose tooth to a firmly attached one.

These results and advantages follow from the fact that the present means and technique include using a cream-like, wipe removable substance to simulate plaque on a row of spaced bodies which are upstanding on a base and adapted to simulate oversized reproductions of natural teeth. The substance is applied to the bodies and a floss simulator, such as a strand of string is manipulated between the bodies, to demonstrate proper flossing technique. One of the bodies may be removable from the base, so that the substance can be applied to the opposing surfaces of the bodies during the application step. Also, the bodies may have a spaced surface thereadjacent, simulating the cramped, crowded condition of the mouth, and one of the instructor's or student's hands may be interposed in the space between the bodies and the surface, during the flossing operation, to simulate the step of flossing under such conditions.

Furthermore, in a related operation, a complementarily sized toothbrush may be manipulated in relation to the bodies, to demonstrate the inability of brushing to remove the plaque simulating substance from the space between the bodies. Again, one of the bodies may be removable from the base, so that the plaque simulating substance can be seen on the opposing surfaces of the bodies.

Preferably, one set of the bodies is relatively closely spaced, and another set is relatively widely spaced. The flossing technique is demonstrated on the relatively widely spaced set of bodies, and the brushing step is carried out on the relatively closely spaced set of bodies.

Additionally, the bodies may have annular grooves about the bases thereof, simulating the recesses in the tissue about the bases of natural teeth. The plaque simulating substance may be applied to one or more grooves, and a complementarily sized toothbrush may be manipulated in relation to the bodies, to demonstrate removal of the plaque simulating substance from the grooves. Preferably, the grooves are progressively deeper and wider lengthwise of the row, the body in a relatively deeper and wider groove is loosely engaged in the base, and the latter body is wobbled to demonstrate the possible consequence of improper cleaning or no cleaning at all. Also, the loosely engaged body may be removable from the base, to demonstrate the ultimate consequence of omitting cleaning and/or cleaning improperly.

A splint may be bridged from the loosely engaged body to another body, to demonstrate the corrective action taken by a dentist. Also, the bodies may have mutually aligned grooves in the tops thereof, and the splint may be inserted in the latter grooves, to demonstrate this further aspect of the corrective action.

As indicated, the means and technique also enable the student to practice the step of "easing" the floss through the contact points between pairs of teeth. In this instance, he employs a plate-like standard, and a floss simulator, such as a strand of string. The plate-like standard is mounted on a base and has a hole therethrough, which opens into one edge of the same, through a narrow slit simulating the contact point between a pair of teeth. The peripheral walls of the hole and the slit approach one another at an angle and the student is told to pass the floss-simulator through the slit in the direction of the hole, and to maintain the floss simulator in contact with the peripheral wall of the hole when the simulator leaves the slit. This simulates the step of avoiding "popping" the floss through the contact point between a pair of teeth, and doing injury to the gum tissue below the point. Instead, the fact of preserving contact with the standard when the floss simulator enters the hole, forces the student to "ease" the simulator through the slit, and after doing this repeatedly, he can carry over the experience to his mouth when he flosses his teeth.

Preferably, there is a series of similar holes in the body of the standard, and each is interconnected with the next by a similar slit through the body of the standard, so that the student can practice easing the floss simulator through a sequence of contact points, just as he would in his mouth. Also, the holes preferably have arcuate walls between slits, so that the student can develop the same arcuate motion that he will use in his mouth, in moving from contact point to contact point, and from surface to surface between each pair of teeth. Usually, the edge of the standard has a part cylindrical groove therein, at the relatively outside end of the first mentioned slit, to assist the student in locating the slit, and to simulate entry into the first "contact point" of the sequence of holes. Usually, too, the first mentioned slit is in the upper edge of the standard.

The plate-like standard may be mounted on the same base as that having the teeth simulator bodies upstanding thereon. In fact, in presently preferred embodiments of the invention, the two sets of teeth simulator bodies are assembled on the base in spaced parallel rows, with the standard upstanding therebetween and preferably in a position where it also functions as a means for defining the roof simulating surface. In this way, the assembly assumes the form of a highly compact demonstrator unit which can also be used by the student as a learning device, or better yet, as a series of learning devices, each of which enables him to understand and develop a separate skill, before the instructor moves on to the next skill.

BRIEF DESCRIPTION OF THE DRAWINGS

These features will be better understood by reference to the accompanying drawings wherein one of the presently preferred embodiments of the invention is illustrated.

In the drawings,

FIG. 1 is perspective view of the demonstrator unit in use;

FIG. 2 is a reverse perspective view of the demonstrator unit;

FIG. 3 is a part removed, end elevational view of the demonstrator unit in use;

FIG. 4 is a cross sectional view of the demonstrator unit, along the line 4—4 of FIG. 2;

FIG. 5 is a side elevational view of the demonstrator unit in use; and

FIG. 6 is a plan view of the demonstrator unit in use.

DESCRIPTION OF THE PREFERRED EMBODIMENT

Referring to the drawings, it will be seen that the demonstrator comprises a slab-like base 2 having rounded corners at its edges and three separate learning devices 4, 6 and 8 standing on the upper surface 10 thereof. The learning device 4 takes the form of three block-like parallelepipedal bodies 12 which are rectangularly cross sectioned in the respective body planes thereof and upended in a row on the surface 10 of the base, with the wider dimensions thereof disposed crosswise of the row and the opposing surfaces 14 thereof spaced apart from one another in parallel planes, to form narrow slots 16 therebetween. The bodies 12 have rounded corners at their upper ends, and in order to secure them to the base, each body has a rectangularly cross sectioned neck 18 formed thereon, which extends downwardly from the lower end of the body and telescopes into a complementarily cross sectioned socket 20 in the surface of the base. The bodies are removably engaged in the surface of the base, therefore, but in other respects they simulate natural teeth, and the fact that the teeth have narrow slots between them. The simulation effect and the purposes for it will be explained shortly.

The surfaces 14 of the block-like simulators 12 may be planar, as seen in FIGS. 1-4, or they may be convexly rounded in both body planes of the simulators, as seen in FIGS. 5 and 6, where they are indicated by numerals 14'.

The learning device 6 takes the form of a plate-like wall 22 having rounded corners on the upper edge 24 thereof and three closely spaced cylindrical holes 26 through the body thereof, the disposition of which is just below the edge 24. The wall is dado bonded into a groove 28 in the surface 10 of the base, and extends crosswise of the surface on a parallel to the row of block-like simulators 12, but in more closely spaced relationship to the other learning device 8 than to the block-like simulators. The holes 26 in the wall are arranged in a row, horizontally thereof, and are interconnected by narrow slits 30 which extend through the wall material between holes, in the axial plane thereof. In addition, the hole 26 at the right-hand end of the row in FIG. 1, opens into the upper edge 24 of the wall through another narrow slit 32 disposed in the vertical axial plane of the hole. The slit 32 has a part-annular groove 34 at the top thereof, which extends crosswise of the edge 24, and in use, the groove 34, the slits 30 and 32, and the holes 26, all have inter-related functions which will be explained shortly.

The third learning device 8 also comprises a set of teeth simulators. However, in this instance, the simulators take the form of peg-like cylindrical bodies 36 which are upended in a row on the surface 10 of the base and engaged in cylindrically cross sectioned sockets 38 in the base. The peg-like simulators 36 are considerably smaller in size than the block-like simulators 12, and they also form considerably wider slots 40 therebetween. Each of the peg-like simulators may also have a groove 42 (FIGS. 5 and 6) across the top thereof, and in such a case, the grooves 42 are aligned with one another lengthwise of the row of simulators. In addition, there are annular grooves 44 formed in the surface 10 of the base about the bottoms of the simulators 36, and the grooves are progressively wider and deeper from body to body in the left-hand direction of FIG. 1. The last simulator in this direction is telescopically engaged in its corresponding socket 38' (FIG. 4), so that the simulator can be removed from the base, but the other simulators are bonded in their sockets so as to be fixed in place. The socket 38' for the last simulator is also slightly oversized so that the simulator can be "wobbled" in place, even while it remains in its socket.

When the demonstrator is put to use in a learning situation, a cream-like, wipe removable substance 46 is used with it, to simulate plaque on the teeth-simulators 12 and 36. Also, a complementarily sized toothbrush 48 is used to demonstrate certain steps of the learning procedure, and a complementarily sized strand of string 50 is used to represent dental floss in other steps. These latter implements may also be used by the student, together with the cream-like substance 46, for purposes of practicing and developing his dental hygiene skills.

The cream-like substance 46 is commonly applied from a pressurized spray dispenser, and may take the form of shaving cream dispensed from a conventional spray can 52 of the same. See FIG. 5. However, other substances may be used to form a plaque simulator, and in addition, other means may be employed to apply the simulator to the teeth simulators. Preferably, however, the plaque simulator should be non-toxic and non-stainable. It should also be wash-removable, either by a solvent or a detergent. It may be colored or neutral, and it may be of various weights and consistencies.

Ordinarily, the instructor will begin the learning process by spraying a portion of the shaving cream on the block-like simulators 12, including removing one or more of them from the base if necessary, in order to spray the cream on the opposing surfaces 14 of the simulators. Then, the toothbrush 48 is given to the student, along with a paper towel, and the student is told to remove the shaving cream from the simulators 12, and to remove it entirely, including from the slots 16 and surfaces 14 between simulators. Of course, the student will quickly note that while he can remove the shaving cream from the surfaces of the simulators (FIG. 6), he cannot do so with respect to the surfaces 14 and the slots 16. Thus, a problem is posed for him: how to clean between the simulators where he finds that he cannot reach the cream with the bristles of the brush.

Next, the instructor demonstrates that the shaving cream between simulators can be removed by grasping the string 50 and using it in the manner of dental floss. See FIG. 3. The instructor may also demonstrate the proper technique for grasping and holding the string (i.e., the floss), as for example, by wrapping ends of the string around the middle fingers of his hands, as one way of securing the string in and between his hands. The instructor will also demonstrate the appropriate technique for flossing, that is, the technique of "sawing" the string back and forth through the slots 16, while engaging it against the respective surfaces 14 of the simulators.

Ultimately, after the student has experimented with a technique for holding the string, and has understood the basics of the technique for flossing, the instructor will move on to the learning device 6 comprising the wall 22. Using this device, he demonstrates the importance of "easing" the string (floss) through the "contact point" 32 or 30 between each pair of teeth, in order to avoid injury to the tissue of the gums. The student is told to keep the string in contact with the wall material at all times, and this forces the student to saw the string gently through each slit 32 or 30, starting with the slit 32, in order to avoid "popping" the string through the slit and out of contact with the wall material. Again, the student is given time to practice and develop this further aspect of proper flossing, and he is also given an opportunity to practice moving the strand of string in arcuate fashion from one tooth to the next, and from one surface to the next between each pair of teeth. See FIG. 3 and the arrows representing the motion which the string undergoes from slit to slit, i.e., from contact point to contact point between the teeth.

Turning next to the learning device 8, the instructor will demonstrate the necessity for "wrapping" the string (floss) about the contour of each tooth, to remove the shaving cream (plaque) in the most effective manner. For example, he may hold the string straight between his hands and floss the first tooth simply with a rectilinear sawing motion. Then, on the second tooth, he will add the feature of wrapping the string about the curvature of the tooth to remove a wider band of the shaving cream (plaque). Again, the student follows the lead of the instructor and proceeds to practice and develop his skills on the simulators 36.

The proximity of the simulators 36 to the wall 22 also enables the instructor to simulate the crowded and cramped conditions under which flossing must be accomplished in the mouth. Yet, the flossing process must be accomplished for complete dental hygiene. Therefore, using the simulators 36, the student can develop the technique, notwithstanding the difficulty posed by the proximity of the wall 22.

In the next step of the procedure, the instructor adds more shaving cream about the rightmost simulator 36 in FIG. 1, and particularly in the groove 44 thereabout. He also points out that if the brush 48 is held perpendicular to the simulator, it is not possible to remove the cream from the groove. Instead, he emphasizes the necessity for angling the brush to the simulators at approximately 45° to reach into the grooves and remove the cream; that is, to reach up under the gum and effectively remove the plaque in actual circumstances. See FIG. 5.

Continuing down the length of the row of simulators 36, the instructor can demonstrate the problem which arises when the gums become more widely detached from the base of the teeth, such that the grooves 44 are wider and deeper. For example, he can demonstrate with the middle and leftmost simulators 36 in FIG. 1, that even where the brush is properly angled to the simulators, it cannot remove the shaving cream (plaque) from the bottom of the grooves 44. And, in the case of the leftmost simulator 36, the instructor can demonstrate the fact that ultimately the tooth may lose its support, so that it can be wobbled in place; or that it may even become detached, so that it is susceptible to being lost entirely, i.e., removed from the base.

Finally, the instructor demonstrates the corrective action that the dentist must take where this latter condition occurs. Using the brush (FIG. 4) or some other rod-like member (FIG. 5), the instructor can simulate the action taken by the dentist in splinting the loose tooth to a firmly anchored tooth, including the necessity for forming slight indentations 42 in the tops of the teeth to take the splint. See FIG. 5 and the bridging of the simulators with the splint in the grooves 42.

What is claimed is:

1. A method of demonstrating dental hygiene procedure comprising applying a wipe removable, plaque simulating substance to a row of spaced bodies which are upstanding on a base and adapted to simulate oversized reproductions of natural teeth, one of said bodies being removed during the application of the plaque simulating substance, so that the substance can be applied to the opposing surfaces of the bodies, and manipulating a floss simulator such as a strand of string, between the bodies, to demonstrate proper flossing technique.

2. the method according to claim 1 wherein the bodies have a spaced surface thereadjacent, simulating the cramped, crowded conditions of the mouth, and one hand is interposed in the space between the bodies and the surface, during the flossing operation, to simulate the step of flossing under such conditions.

3. The method according to claim 1 further comprising manipulating a complementarily sized toothbrush in relation to the bodies to demonstrate the inability of brushing to remove the plaque simulating substance from the space between the bodies.

4. The method according to claim 3 and the step of removing one of said bodies from the base after the brushing step, so that the plaque simulating substance can be seen in the opposing surfaces of the bodies.

5. The method according to claim 3 wherein one set of the bodies is relatively closely spaced and another set if relatively widely spaced, and the flossing technique is demonstrated on the relatively widely spaced set of bodies, and the brushing step is carried out on the relatively closely spaced set of bodies.

6. A method of demonstrating dental hygiene procedure comprising applying a wipe removable, plaque simulating substance to a row of spaced bodies which are upstanding on a base and adapted to simulate oversized reproductions of natural teeth, said bodies having annular grooves about the bases thereof, simulating the recesses in the tissue about the bases of natural teeth, the plaque simulating substance being applied to one or more of said grooves, and manipulating a complementarily sized toothbrush in relation to the bodies to demonstrate removal of the plaque simulating substance from the grooves.

7. The method according to claim 6 wherein the grooves are progressibely deeper and wider lengthwise of the row, the body in a relatively deeper and wider groove is loosely engaged in the base, and the latter body is wobbled to demonstrate the consequences of improper cleaning or no cleaning at all.

8. The method according to claim 7 wherein the loosely engaged body is also removable from the base, and said body is removed from the base to demonstrate the ultimate consequences of omitting cleaning and/or improper cleaning.

9. The method according to claim 7 wherein a splint is bridged from the loosely engaged body to another body, to demonstrate the corrective action taken by a dentist.

10. The method according to claim 9 wherein the bodies have mutually aligned grooves in the tops thereof, to receive a splint bridged from the loosely engaged body to another body to demonstrate this further aspect of the corrective action.

11. A method of practicing dental hygiene and particularly flossing, using a plate-like standard having a hole therethrough, which opens through a narrow slit to one edge of said standard, simulating the contact point between a pair of teeth, the peripheral walls of the hole and the slit approaching one another at an angle, comprising passing a floss simulator through the slit in the direction of the hole, and maintaining the floss simulator in contact with the peripheral wall of the hole when the simulator leaves the slit, to simulate the step of cleaning that portion of the teeth below said contact point without "popping" the floss through said contact point and doing injury to the gum tissue below said point.

12. Means for demonstrating dental hygiene procedure comprising a base, a first set of spaced-apart blocklike bodies which are upstanding on the base and adapted to simulate oversized reproductions of natural teeth, at least one of said bodies being removable from said base, a second set of bodies, one set of the bodies being relatively closely spaced and another set being relatively widely spaced, a wipe removable, plaque simulating substance, and means for applying the substance to surfaces of said bodies, so that a toothbrush or floss simulating means can be manipulated in relation to the bodies, to demonstrate brushing and/or flossing of teeth of various configurations.

13. The means according to claim 12 wherein the bodies have a spaced surface thereadjacent, simulating the cramped, crowded conditions posed by the roof of the mouth, so that one hand can be interposed in the space between the bodies and the surface, during the flossing operation, to simulate the step of flossing under such conditions.

14. Means for demonstrating dental hygiene procedure comprising a base and a row of spaced bodies which are upstanding on the base and adapted to simulate oversized reproductions of natural teeth, said bodies having annular grooves about the bases thereof, simulating the recesses in the tissue about bases of natural teeth, said grooves being progressively deeper and wider lengthwise of the row so that a plague simulating substance can be applied to one or more grooves, and a complementarily sized toothbrush can be manipulated in relation to the grooves, to demonstrate removal of the plaque simulating substance from the same, the body in a relatively deeper and wider groove being loosely engaged in the base.

15. The means according to claim 14 wherein the loosely engaged body is also removable from the base, so that said body can be removed from the base to demonstrate the ultimate consequence of omitting brushing and/or improper brushing.

16. The means according to claim 14 wherein the bodies have mutually aligned grooves in the tops thereof, to receive a splint bridged from the loosely engaged body to another body, to demonstrate the corrective action taken by a dentist.

17. The means according to claim 14 further including a plate-like standard upstanding upon said base and spaced apart from said row of spaced bodies to simulate the limited space available in a human mouth for dental hygiene manipulation.

18. The means of claim 17 wherein said plate-like standard has a hole therethrough, which opens through a narrow slit into one edge of the standard, said slit simulating the opening between a pair of teeth, the peripheral walls of the hole and the slit approaching one another at an angle, whereby passing a floss simulator through the slit in the direction of the hole, and maintaining the simulator in contact with the peripheral wall of the hole when the simulator leaves the slit, simulates the step of avoiding "popping" the floss through the contact point between a pair of teeth, and doing injury to the gum tissue below said point.

19. The means according to claim 18 wherein there is a series of similar holes in the body of the standard, and each hole is interconnected with the next by a similar slit, so that the floss simulator can be passed through a sequence of contact points, just as would be done in the mouth.

20. The means according to claim 18 wherein the edge of the standard has a part cylindrical groove therein, at the relatively outside end of the slit, to assist in locating the slit, and to simulate entry into the contact point.

21. The means according to claim 19 wherein the holes have arcuate walls between slits, so that the floss simulator can be put through the same arcuate motion used in the mouth, in moving from contact point to contact point, and from surface to surface between each pair of teeth.

22. The means according to claim 19 wherein the slit is in the upper edge of the standard.

23. Means for demonstrating dental hygiene procedure and/or practicing the same, comprising a base, a row of spaced bodies upstanding on the base and adapted to simulate oversized reproductions of natural teeth, and a plate-like standard upstanding on the base, in spaced relationship to the row of teeth simulator bodies, and having a hole therethrough, which opens into the upper edge of the standard through a narrow slit simulating the contact point between a pair of teeth, the peripheral walls of the hole and the slit approaching one another at an angle, and the standard being positioned adjacent the teeth simulator bodies so that when a floss simulator such as a strand of string, is manipulated between the bodies, to demonstrate and/or practice flossing, a surface of the standard simulates the cramped, crowded conditions posed by the roof of the mouth.

24. The means according to claim 23 wherein there are two spaced parallel rows of the bodies upstanding on the base, having different spacings therebetween from row to row, and the standard is upstanding between the rows.

* * * * *